United States Patent [19]

Adachi

[11] Patent Number: 4,571,382

[45] Date of Patent: * Feb. 18, 1986

[54] PROCESS FOR DETERMINING TUMOR-ASSOCIATED GLYCOLINKAGE AND METHOD FOR DIAGNOSIS OF CANCER

[75] Inventor: Masakazu Adachi, Gunma, Japan

[73] Assignee: Otsuka Pharmaceutical Co., Ltd., Japan

[*] Notice: The portion of the term of this patent subsequent to Jan. 21, 2000 has been disclaimed.

[21] Appl. No.: 288,445

[22] Filed: Jul. 30, 1981

[30] Foreign Application Priority Data

Jul. 30, 1980 [JP] Japan .............................. 55-104786

[51] Int. Cl.$^4$ ............................................. G01N 33/54
[52] U.S. Cl. .......................................... 435/7; 435/188; 436/501; 436/503; 436/504; 436/513; 436/527; 436/529; 436/530; 436/531; 436/528; 436/524; 436/539; 436/542; 436/813; 436/827
[58] Field of Search .................... 435/4, 7, 177, 178, 435/179, 180, 181, 188; 424/1, 1.5, 8, 12; 436/501, 503, 504, 518, 524, 527, 528, 529, 530, 531, 536, 538, 539, 542, 813, 827, 513

[56] References Cited

U.S. PATENT DOCUMENTS

| | | | |
|---|---|---|---|
| 4,016,043 | 4/1977 | Schuurs et al. | 435/7 |
| 4,105,598 | 8/1978 | Yen et al. | 435/7 |
| 4,132,769 | 1/1979 | Osther | 424/12 |
| 4,146,603 | 3/1979 | Davidson et al. | 424/12 |
| 4,147,764 | 4/1979 | Levy et al. | 424/1 |
| 4,160,817 | 7/1979 | Bucooaz et al. | 424/12 |
| 4,196,186 | 4/1980 | Bogoch | 436/503 |
| 4,235,867 | 11/1980 | Thoma | 436/531 |
| 4,289,747 | 9/1981 | Chu | 435/7 |
| 4,334,017 | 6/1982 | Plotkin et al. | 23/230 B |
| 4,389,392 | 6/1983 | Adachi | 436/501 |

FOREIGN PATENT DOCUMENTS

154660 11/1981 Japan ....................... 435/4

OTHER PUBLICATIONS

23 230 B
Nicolson et al., Biochemistry, 13(1), 196–204 (1974).
Lotan et al., J. Biol. Chem., 250(21), 8518–8523 (1975).
Prieels et al., PNAS USA, 75(5), 2215–2219 (1978).
Kabat, *Methods in Enzymology, Immunochemical Techniques,* vol. 70, Academic Press, New York, 3, 31–35 (1980).
Lotan et al., Biochem. Biophys. Res. Comm., 62(1): 144–150 (1975).
Burnet et al., Br. J. Exp. Pathol., 27: 228–236 (1946).
Greenwood et al., Biochem J., 89, 114–123 (1963).
Hunter et al., Nature, 94(4827), 495–496 (1962).
Karol et al., PNAS USA, 57: 713–720 (1967).
Erlanger et al., Acta Endocrinol. Suppl., 168: 206–221 (1972).
Gonatas et al., Chemical Abstracts, 80: 12154t (1974).
Pereira et al., Carbohy. Res., 51: 107–118 (1976).

*Primary Examiner*—Esther M. Kepplinger
*Attorney, Agent, or Firm*—Sughrue, Mion, Zinn, Macpeak and Seas

[57] ABSTRACT

Determination of tumor-associated glycolinkage (TAG) by:

(1) competitively reacting body fluid TAG to be measured and a definite quantity of insolubilized TAG or TAG-like material with a definite quantity of lectin labelled with a labelling agent, separating the insolubilized TAG or insolubilized TAG-like material bound to the labelled lectin and unbound labelled lectin from each other, and measuring the labelling agent activity of either of them;

(2) competitively reacting the material to be measured and a definite quantity of TAG or TAG-like material labelled with a labelling agent with a definite quantity of lectin or insolubilized lectin, separating the labelled TAG or labelled TAG-like material bound to lectin or insolubilized lectin and unbound labelled TAG or TAG-like material from each other, and measuring the labelling agent activity of either or them; or (3) reacting the material to be measured with the insolubilized lectin to form a TAG-insolubilized lectin complex, reacting this complex with a definite quantity of the labelled lectin, separating the complex bound to the labelled lectin and unbound labelled lectin from each other, and measuring the labelling agent activity of either of them.

20 Claims, 11 Drawing Figures

TAG LEVELS OF PATIENTS WITH CANCERS

FIG. 7(d)

TAG LEVELS OF PATIENTS WITH DISEASE
OTHER THAN CANCERS AND OF PREGNANT WOMEN n moles/mℓ eq. galactose

| | | 60  100     200     300  500 |
|---|---|---|
| DIABETIS MELLITES | | ⋯⋯• • |
| NEPHRITIS | | ••• ⋯• |
| CYSTITIS | | • |
| URETERAL STONE | | • |
| CHOLECYSTITIS | | • |
| GALLSTONE | | ••• •           • |
| COLLAGEN D. | | ••• • |
| PREGNANCY | E | •• • |
| | M | •   •• |
| | L | • |
| DEPRESSION | | • •• |
| ALLERGIC CORYZA | | • |
| PURPURA | | •• |

PROCESS FOR DETERMINING TUMOR-ASSOCIATED GLYCOLINKAGE AND METHOD FOR DIAGNOSIS OF CANCER

BACKGROUND OF THE INVENTION

This invention relates to a process for determining tumor-associated glycolinkage (hereinafter abbreviated as TAG) in body fluid of a mammal, i.e., TAG including glycoproteins, glycopeptides, glycolipids and/or sugars containing galactose-($\beta 1 \rightarrow 3$ or $\beta 1 \rightarrow 4$)-N- acetylglucosamine or galactose-($\beta 1 \rightarrow 3$ or $\beta 1 \rightarrow 4$)-N-acetyl- galactosamine terminus which increases with the proliferation of undifferentiated cells, particularly tumorous cells or cancerous cells, and to a method for diagnosing of cancer by determining the above-described TAG.

As a method for diagnosing cancer, it has been conducted to measure a specific glycoprotein which is specifically yielded in patients suffering cancers. This method mainly utilizes the antigenicity of protein moiety of the glycoprotein; for example, there are known diagnosis of primary cancerof the liver by measuring $\alpha_1$-fetoprotein and diagnosis of cancer of a digestive organ, particularly cancer of the rectum, by measuring CEA ["Igaku no Ayumi (Progress in Medicine)", Vol. 106, No. 5, Fifth Saturday Special Issue, pp. 235-250 (1978)]. However, these diagnostic methods are comparatively limited in their applicability, and there has been desired a diagnostic method for diagnosing a wide variety of cancers.

No methods of diagnosing cancers by utilizing the binding specificity of sugar residue of tumor-associated glycolinkage have so far been known.

It has been found that body fluid of a patient with cancer contains TAG yielded by undifferentiated cells (mainly cancerous cells) and released into the fluid, and that TAG is considerably different in sugar chain structure, sugar chain length, and kind of constituent sugar residue and, as a result of extensive investigations, it has been found that this TAG includes glycoproteins, glycopeptides, glycolipids and/or sugars having galactose-($\beta 1 \rightarrow 3$ or $\beta 1 \rightarrow 4$)-N-acetylglucosamine terminus or galactose-($\beta 1 \rightarrow 3$ or $\beta 1 \rightarrow 4$)-N-acetylgalactosmine terminus, that this TAG specifically combines with lectin, and that presence or absence of cancerous cells, degree of proliferation, prosperity and decay of the cells, and the like can be known by reacting body fluid TAG with lectin, through which cancer can be diagnosed. The present invention has been achieved based on the above finding.

SUMMARY OF THE INVENTION

It is, therefore, an object of the present invention to provide a process for measuring body fluid TAG level according to a competitive process or a sandwiching process. and a method of diagnosing cancer by measuring TAG level.

BRIEF DESCRIPTION OF THE DRAWINGS

FIG. 7 shows TAG levels of cancerous patients measured according to the competitive process of the present invention.

FIG. 7d shows TAG levels of patients suffering various diseases other than cancers or of pregnant women.

DETAILED DESCRIPTION OF THE INVENTION

Figure 1:
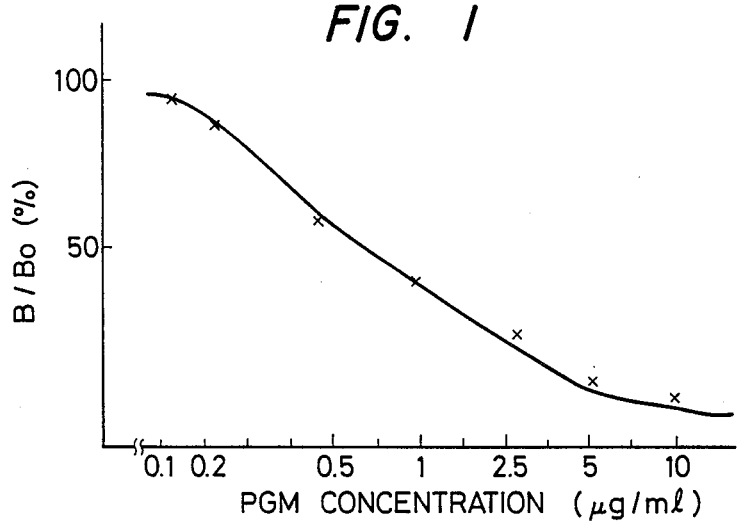
FIG. 1 shows a standard curve obtained by the competitive process of the present invention.

The above-described object of the present invention can be attained by one of the following processes of:

(1) competitively reacting body fluid TAG to be measured (hereinafter referred to as the material to be measured) and a definite quantity of insolubilized TAG or TAG-like material (hereinafter referred to as insolubilized TAG or insolubilized TAG-like material) with a definite quantity of lectin labelled with a labelling agent (hereinafter referred to as labelled lectin), separating the insolubilized TAG or insolubilized TAG-like material bound to the labelled lectin and unbound labelled lectin from each other, and measuring the labelling agent activity of either of them;

(2) competitively reacting the material to be measured and a definite quantity of TAG or TAG-like material labelled with a labelling agent (hereinafter referred to as labelled TAG or labelled TAG-like material) with a definite quantity of lectin or insolubilized lectin (hereinafter referred to as insolubilized lectin), separating the labelled TAG or labelled TAG-like material bound to lectin or insolubilized lectin and unbound labelled TAG or TAG-like material from each other, and measuring the labelling agent activity of either or them; and (3) reacting the material to be measured with the insolubilized lectin to form a TAG-insolubilized lectin complex, reacting this complex with a definite quantity of the labelled lectin, separating the complex bound to the labelled lectin and unbound labelled lectin from each other, and measuring the labelling agent activity of either of them.

As the body fluid to be used in the present invention, various body fluids can be employed, among which are blood, cell tissue fluid, lymph fluid, thorax fluid, abdominal fluid, amniotic fluid, gastric juice, urine, pancreatic juice, cerebrospinal fluid, and saliva. Of these, the use of blood in the form of serum or blood plasma is particularly preferred. The quantity of body fluid to be used for the determination ranges from about 1 to about 10 ml, preferably from 2 to 5 ml. This body fluid may further be purified to isolate the glycolinkage containing materials such as glycoproteins, glycopeptides, glycolipids and/or saccharides.

As a process for obtaining a material containing the glycolinkage in high content from the body fluids, conventionally known means for extraction or separation of glycolinkage, such as salting out, precipitation, extraction, centrifugation, dialysis, molecular sieve method, inactivation of enzyme, or a combination thereof is employed. More particularly, such fraction is prepared by adding sulfosalicylic acid, trichloroacetic acid or zinc sulfate to serum or plasma or heating serum or plasma, filtering off a precipitate thus-formed to remove albumin, immunoglobulin, etc., and conducting dialysis.

In the determination process of the present invention, body fluid samples which have been collected except for blood can be used as they are as test samples (hereinafter abbreviated as "samples"). However, in order to prevent samples from being denatured and accelerate the reaction with lectin, lower-sugar-containing proteins such as bovine serum albumin (BSA) or the like may be added to the samples as protective proteins. Further, in some cases, addition of a suitable amount of protective protein to a sample from which albumin, immunoglobulin or the like has been removed provides good results. And, with a blood sample, serum obtained according to a known serum-collecting process or plasma obtained according to a plasma-collecting process using an anticoagulant such a heparin, EDTA, citric acid or the like can be used as a sample, with the serum sample collected and prepared by using heparin as an aticoagulant being particularly preferred. Where the TAG level is relatively high as with ascites, samples may, if desired, be diluted with a proper buffer solution.

As the lectin to be used in the present invention, there are illustrated those which can combine specifically with galactose-($\beta 1 \rightarrow 3$ or $\beta 1 \rightarrow 4$)-N-acetylglucosamine or galactose-($\beta 1 \rightarrow 3$ or $\beta 1 \rightarrow 4$)-N-acetylgalactosamine [*J.B.C.*, 250, 8518-8523 (1975); *Biochem. Biophys. Res. Comm.*, 62, 144 (1975); *Z. Immunitaetsforch*, 138, 423-433 (1969); *Br. J. Exp. Pathos.*, 27, 228-236 (1946); *Proc. Natl. Acad. Sci.*, USA, 75, No. 5, 2215-2219 (1978); *Biochemistry*, 13, 196-204 (1974); *Carbohydrate Research*, 51, 107-118 (1976)], such as peanut lectin, castor bean (Ricinus communis) lectin, etc.

As the labelling material for labelling lectin and TAG or TAG-like material, there are illustrated various enzymes, various fluorescent materials, and various radioactive materials, etc. Such enzymes include, for example, glucoamylase, glucose oxidase, peroxidase, alkaline phosphatase, $\beta$-galactosidase, and active fragment of hermoctapeptide, etc., fluorescent materials include, for example, fluorescein, fluorescein isothiocyanate, rhodamine, dansyl chloride (i.e., 5-dimethylamino-1-naphthalenesulfonyl chloride), etc., and radioactive materials include, for example, radioactive iodine (e.g., $^{125}I$, $^{131}I$, etc.), radioactive tritium, etc.

In the present invention, the term "TAG-like material" indicates galactose-($\beta 1 \rightarrow 3$ or $\beta 1 \rightarrow 4$)-N- acetylglucosamine, galactose-($\beta 1 \rightarrow 3$ or $\beta 1 \rightarrow 4$)-N-acetylgalactosamine, and sugar derivatives containing such glycolinkage at a terminal end. As such sugar derivatives, there are illustrated, for example, glycoprotein of human gastric mucin, glycoprotein obtained by removing terminal fucose from sulfated glycoprotein of porcine gastric mucous membrane, human IgG glycoprotein or the asialo derivative thereof, bovine IgG glycoprotein, asialo derivative of glycoprotein of porcine thyroglogulin glycolinkage B, glycoprotein of ovomucoid $\beta$-subunit, glycoprotein B-1 of human IgE or the asialo derivative thereof, asialo derivative of glycoprotein B-2 or B-3 of human IgE and asialo derivative of glycoprotein II-C of human IgA$_1$, asialo derivative of glycoprotein II-B or II-A of human IgA$_1$, asialo derivative of human transferrin glycoprotein, asialo derivative of bovine fetuin glycoprotein, deasialo derivative of glycoprotein participating in uptake of asialo glycoprotein of rabbit liver cell protoplasmic membrane, sulfated glycoprotein of procine gastric mucosa, asialo derivative of human $\alpha_1$ acidic glycoprotein, asialo derivative of glycofolin, glycoprotein or glycopeptide of T-antigen or the like, described in "Biochemical Data Book I" (compiled by Japanese Chemical Society and published by Tokyo Kagaku Dojin, Nov. 26, 1979), pp. 503–510; and asialo $GM_1 = AM_1$ and glycolipids of bovine erythrocyte described in the same literature, pp. 840–841. Of these, asialo derivative of bovine fetuin glycoprotein, sulfated glycoprotein of porcine gastric mucosa, sulfated glycoprotein of human gastric mucosa, and asialo derivative of human $\alpha_1$ acidic glycoprotein are preferred.

Insolubilized TAG, insolubilized TAG-like material, and insolubilized lectin are prepared by chemically or physically reacting TAG, TAG-like material or lectin with an insoluble carrier. As such insoluble carrier, there are illustrated cellulose powder, Sephadex, Sepharose, polystyrene, filter paper, carboxymethyl cellulose, ion-exchange resin, dextran, plastic film, plastic tube, nylon, glass beads, silk, polyamine-methyl vinyl ether-maleic acid copolymer, amino acid copolymer, ethylene-maleic acid copolymer, etc. Insolubilization can be effected by a covalent bond-forming process [i.e., a diazo process, a peptide process (e.g., an acid amide derivative process, a carboxy chloride resin process, a carbodiimide resin process, a maleic anhydride derivative process, an isocyanate derivative process, a cyanogen bromide-activated polysaccharide process, a cellulose carbonate derivative process, a process using a condensing agent, etc.), an alkylating process, a carrier-binding process using a cross-linking agent such as glutaraldehyde, hexamethylene isocyanate, etc.], a carrier binding process accordingto Ugi reaction, and the like, an ion-binding process using such carrier as ion-exchange resin; and a physically absorbing process using porous glass such as glass beads as a carrier. Of these, the cyanogen bromide-activated polysaccharide process of the covalent bond-forming process and the carrier-binding process using a cross-linking agent are preferred. According to the cyanogen bromide-activated polysaccharide process, insolubilized TAG, insolubilized TAG-like material or insolubilized lectin can be obtained by reacting TAG, etc., with a 10- to 1,000-fold amount of a cyanogen bromide-activated carrier in a suitable solvent at 0° to 40° C., preferably at 20° to 30° C., for 2 to 4 hours.

Also, insolubilized TAG, etc., can be prepared according to a radiation-induced polymerization process. That is, an aqueous dispersion of a polymerizable monomer containing TAG or TAG-like material is prepared and irradiated with light or ionizing radiation to polymerize said monomer. As a means to prepare the aqueous dispersion, a hydrophobic polymerizable monomer [A] is dispersed in a 0.1 to 5 wt % aqueous solution of water-soluble polymer [B]. Alternatively, hydrophilic polymerizable monomer [C] or a mixture of hydrophobic polymerizable monomer [A] and hydrophilic polymerizable monomer [C] is dispersed in a 3 to 20 wt % saline aqueous solution, or hydrophobic polymerizable monomer [A] is dispersed in an aqueous solution containing 0.01 to 5 wt % surfactant [D]. When the thus-obtained dispersion is irradiated with light or ionizing radiation, the polymerizable monomer present therein as a dispersed phase is polymerized to form a polymeric matrix for TAG or the like. If desired, this may be formed into a sheet or particles.

As the specific examples of the hydrophobic polymerizable monomer [A], there are illustrated glycidyl methacrylate, ethylene glycol dimethacrylate, diethylene glycol dimethacrylate, triethylene glycol dimethacrylate, trimethylolpropane trimethacrylate, polyethylene glycol 200 dimethacrylate, dipropylene glycol dimethacrylate, 1,4-butylene glycol dimethacrylate, 1,6-hexane glycol dimethacrylate, methoxydiethylene glycol dimethacrylate, methyl methacrylate, ethyl methacrylate, butyl methacrylate, and the corresponding acrylates thereof. In general, any water-insoluble monomer that can be polymerized by irradiation with light or radiation can be used regardless of the kind thereof.

As the specific examples of the hydrophilic polymerizable monomer [C], there are illustrated 2-hydroxyethyl methacrylate, methoxytetraethylene glycol methacrylate, methoxypolyethylene glycol 400 methacrylate, methoxypolyethylene glycol 1000 methacrylate, polyethylene glycol 400 dimethacrylate, polyethylene glycol 600 dimethacrylate, and the corresponding acrylates thereof and methacrylic acid, acrylamide, N-vinyl-2-pyrrolidone, etc. In general, any water-soluble monomer that can be polymerized by irradiation with light or radiation can be used regardless of the kind.

As the specific examples of the water-soluble polymer [B], there are illustrated polyvinyl pyrrolidone, polymethacrylic acid, polyacrylic acid, polyvinyl alcohol, hydroxypropyl cellulose, gum arabic, etc.

As the specific examples of the surfactant [D], there are illustrated sodium laurylsulfate, potassium oleate, sodium oleate, sorbitan monolaurate, sorbitan monostearate, sorbitan monooleate, propylene glycol monolaurate, oleic acid, sodium dodecylbenzenesulfonate, etc. However, any surfactant that can retain the polymerizable monomer or TAG or TAG-like material dissolved in the polymerizable monomer within the micelle thereof can be used regardless of the kind thereof.

Radioactive material-labelled TAG, radioactive material-labelled TAG-like material, and radioactive material-labelled lectin can be prepared by introducing into TAG, TAG-like material or lectin a radioactive iodine atom such as $^{125}I$ or $^{131}I$. Introduction of radioactive iodine is effected by ordinary iodizing processes, for example, an oxidative iodination process using chloramine T [*Nature*, 194, p. 495 (1962); *Biochem. J.*, 89, p. 114 (1963)]. That is, such iodination is conducted in a suitable solvent [e.g., buffer solution of pH 6–8, preferably 0.2M phosphate buffer solution (pH 7)] at about room temperature for 5 to 60 seconds in the presence of chloramine T. Radioactive iodine and chloramine T are preferably used in amounts of 1 to 5 mCi and 10 to 100 nano moles, respectively, per nano mole of tyrosine contained in TAG or the like. The thus-labelled TAG or the like is isolated and separated in a conventional manner and stored, if necessary, in the lyophilized form.

Enzyme-labelled TAG, enzyme-labelled TAG-like material, and enzyme-labelled lectin can be prepared by a known coupling process [for example, B. F. Erlanger et al., *Acta. Endocrinol. Suppl.*, 168, 206 (1972) and M. H. Karol et al., *Proc. Nat. Acad. Sci.* USA, 57, 713 (1967)]. That is, TAG or the like is reacted with enzyme in a buffer solution of pH 4–6 (e.g., 1 mM acetate buffer solution (pH 4.4)) at room temperature for 2 to 5 hours in the presence of an oxidizing agent such as $NaIO_4$ followed by reduction with $NaBH_4$ or the like. Enzyme is used in an amount of 1 to 3 mols per mol of TAG or the like. The oxidizing agent is used in an amount of 100 to 300 moles per mol of TAG or the like, and the reducing agent in an amount of 1 to 2 mols.

Fluorescent material-labelled TAG, fluorescent material-labelled TAG-like material, and fluorescent material-labelled lectin are prepared by reacting TAG or the like with a known fluorescent material such as fluorescein isothiocyanate (FITC) or tetramethylrhodamine isothiocyanate (RITC) in water or a physiological saline solution of pH 6–8 at 0° C. to room temperature, preferably at room temperature, for 0.5 to 3 hours (fluorescent antibody process; "Ikagaku Jikkenho Koza, No. 4", pp. 263–270). The fluorescent material is preferably used in an amount of 1/50 of TAG or the like.

The determining process of the present invention by the competitive process or sandwiching process will be described below.

In the two processes, the reactions are effected in a suitable solvent at 45° C. or lower, preferably 4° to 40° C., more preferably 20° to 40° C. As such solvent, those which do not adversely affect the reaction of TAG or TAG-like material with lectin, such as water and buffer solutions of pH 6 to 7.8 (e.g., 0.1 to 0.3M tris-hydrochloric acid buffer solution (pH about 7.5), 0.1M phosphate buffer solution (pH about 7.4), etc.) are preferred. The reactions are conducted for 5 to 40 hours, preferably 15 to 25 hours.

Separation of the TAG (or TAG-like material) bound to lectin and unbound lectin or TAG (or TAG-like material) from each other can be conducted in a known manner. That is, where insolubilized TAG (or TAG-like material) or insolubilized lectin is used, mere separation of solid phase from liquid phase (by centrifugation, filtration or decantation) suffices and, in other cases, there may be utilized chromatography, electrophoresis, salting out, fractionation, dialysis, gel filtration, adsorption, or the combination thereof, or a separation process using agar gel, agarose gel or polyacrylamide gel (Japanese Patent Application (OPI) No. 151263/80) (the term "OPI" as used herein refers to a "published unexamined Japanese patent application").

Labelling agent activity of the thus-separated product is measured by selecting a proper method depending upon the kind of the labelling agent. For example, with enzyme, a proper enzyme substrate for colorimetric analysis system, emission analysis system or fluorescence analysis system is selected and, if desired, a dye, luminous agent or coloring agent is used to measure the enzyme activity or, where a fluorescent agent or a radio-active material is used as a labelling agent, the fluorescence intensity or radioactivity is measured. Thus, reacted or unreacted TAG, TAG-like material or lectin can be determined, from which the quantity of the material in question can be known.

As has been described above, the present invention enables one to advantageously determine TAG in body fluid. And, from the thus-obtained TAG quantity can be diagnosed cancer of any stage of from early stage to the last stage. This process is particularly useful for discovering cancer in an early stage. Further, since glycolinkage is determined in the present invention, this diagnosing method can be utilized for a wider scope of cancers than the conventional andibody-utilizing processes (α-fetoprotein, CEA, etc.) mainly determining protein moiety, such as gastric cancer, cancer of the breast, carcinoma of the colon, rectal cancer, ovarium cancer, cancer of the mouth, cancer of the tongue, laryngeal cancer, prostatic cancer, liposarcoma, malignant melanoma, uterine cancer, stomach-primary sarcoma, etc.

Further, the process of the present invention is characterized in that it is highly specific to cancers and does not cross-react with determinants of similar substances in body fluids of pregnant women and of patients who suffer diseases other than cancers such as gastritis, gastric ulcer, duodendal ulcer, colitis, pancreatitis, diabetes mellitus, nephritis, cystitis, ureteral stone, cholecystitis, gallstone, collagen disease, cerebro malacia, apoplexy, angina pectoris, heart failure, myocardial infarction, hypertension, arteritis, depression, allergic coryza, purpura, pneumonia, pulmonary pneumatosis, bronchitis, asthma, acute hepatitis, chronic hepatitis, etc.

Still further, the present invention enables one to determine galactose-($\beta1\rightarrow3$ or $\beta1\rightarrow4$)-N-acetylglucosamine or galactose-($\beta1\rightarrow3$ or $\beta1\rightarrow4$)-N-acetylgalactosamine, or sugars or sugar derivatives (e.g., glycoproteins, glycopeptides, glycolipids, glycoterpene, glycosteroids, etc.) having said glycolinkage at the terminal end.

The present invention will now be described in more detail by the following non-limiting examples of the preferred embodiments of the present invention.

EXAMPLE 1

(i) Activation of Peroxidase 5 mg of peroxidase (of horseradish origin) was dissolved in 1 ml of a 0.3M sodium hydrogencarbonate aqueous solution. 0.1 ml of a 0.1M fluorodinitrobenzene ethanol solution was added to the resulting solution, to which after gently stirring for 1 hour at room temperature, was added 0.1 ml of a 0.06M $NaIO_4$ solution followed by gently stirring for 30 minutes at room temperature. Further, 1 ml of a 0.16M ethylene glycol was added to the reaction mixture, and the resulting solution was gently stirred at room temperature for 1 hour. Then, the solution was dialyzed against 0.01M carbonic acid-sodium hydrogencarbonate buffer solution (pH 9.5) at 4° C. for one day and one night.

(ii) Process for Labelling Lectin with Peroxidase (Lectin-Peroxidase)

5 mg of peanut lectin was dissolved in 3 ml of activated peroxidase obtained in (i), and gently stirred at room temperature for 2-3 hours to react. 5 mg of $NaBH_4$ was added thereto and reacted at 4° C. for 3 hours. Thereafter, this solution was dialyzed against a 0.1M trishydrochloric acid buffer solution (pH 7.4) for one day and one night, and subjected to Sephadex G 150 gel column chromatography (eluent: 0.1M trishydrochloric acid buffer solution; pH 7.4) to conduct gel filtration. Each fraction was measured at $OD_{280}$ and $OD_{403}$ and fractions having the peaks for $OD_{280}$ and $OD_{403}$ were collected.

(ii') Process for Preparing Purified Lectin-Peroxidase 20 ml of lectin-peroxidase obtained in (ii) above was charged on galactose-agarose (AGALACTOPYRANOSYL AGAROSE®) produced by P.L.LaB. USA) and washed with 200 ml of physiological saline solution. The column was eluted with 0.2M NaCl solution containing 0.5M lactose and the first 10 ml fraction having the peaks for $OD_{280}$ and $OD_{403}$ were collected, which were dialyzed against physiological saline solution for one day and one night to obtain purified lectin-peroxidase. The protein content of the product which was measured according to Lowry method (Lowry O. H., et al, *J. Biol. Chem.*, 193, p. 265 (1951)) is about 1 g. The purified lectin-peroxidase was lyophilized.

(iii) Process for Preparing Insolubilized Lectin (Process for Preparing PNA-Agarose)

15 g of CNBr-activated agarose was suspended in 3 liter of 0.001N hydrochloric acid and, after allowing to stand for 30 minutes, washed with 1 liter of 0.1M sodium hydrogencarbonate (pH 8.5) on a glass filter. Thus, there was obtained a total of about 50 ml of activated agarose. This was suspended in 200 ml of 0.1M sodium hydrogencarbonate (pH 8.5), and 5 ml of a 0.01M phosphate buffer solution (pH 7.7) containing 50 mg of peanut lectin (hereinafter abbreviated as PNA) was added thereto followed by reacting at room temperature for 2 hours with stirring at times. After completion of the reaction, the reaction solution was washed on a glass filter, and the reaction product was added to 200 ml of a 1M monoethanolamine solution (pH 8.5) and reacted for 2 hours at room temperature. Thereafter, the reaction product was washed on a glass filter with 1 liter of a 0.1M acetic acid buffer solution (containing 0.5M NaCl) and 1 liter of a 0.1M boric acid buffer solution (containing 0.5M NaCl) alternately three times.

(iv) Process for Preparing TAG-Like Material 1 g of sulfated glycoprotein of porcine gastric mucosa (hereinafter abbreviated as PGM) was suspended in 100 ml of a 0.5M phosphate buffer solution (pH 7.0), and a 1N NaOH aqueous solution was dropwise added thereto to adjust the pH to 11. After stirring for 30 minutes at room temperature, the mixture was centrifuged for 10 minutes at 3,000 rpm, and the supernatant was adjusted to pH 7.0 with 1N HCl followed by again centrifuging for 10 minutes at 3,000 rpm. The supernatant was dialyzed against 10 liter of a 0.01M phosphate buffer solution (pH 7.0) overnight to obtain purified TAG-like material (pure PGM).

(iv') Process for Preparing TAG-Like Material

Alternatively, crude PGM (100 g) was added to 1 liter of distilled water and allowed to stand overnight. After the mixture was dialyzed against distilled water overnight it was centrifuged (100,000 g×1 hour). Then the supernatant was collected and lyophilized to obtain about 5.5 g of purified PGM.

(v) Process for Preparing Labelled TAG (a) Labelling with an Enzyme (PGM-Peroxidase)

4 mg of peroxidase of horseradish origin (HRPO) (0.1 μM) was dissolved in 1 ml of distilled water. To this was added 0.2 ml of 0.1M $NaIO_4$ and, after stirring at room temperature for 20 minutes, the solution was dialyzed against 1 mM acetic acid buffer solution (pH 4.4) for one day and one night to remove unreacted $NaIO_4$. To this dialyzed reaction solution was added about 60 μl of a 0.2M hydrogencarbonate buffer solution (pH 9.5) to adjust the pH of the solution to 9.0. Then, to this solution was immediately added 0.6 ml of PGM (10 mg/ml) dissolved in a 0.01M hydrogencarbonate buffer solution (pH 9.5), mixed for 2 hours at room temperature, and 0.1 ml of a 4 mg/ml of $NaBH_4$ solution in distilled water was added thereto followed by allowing to stand at 4° C. for 2 hours. Further, this solution was dialyzed against a 0.01M phosphate buffer solution (pH 7.5) for one day and one night, and purified using Sephadex G-200 (1.5×150 cm) to obtain pure PGM-peroxidase (PGM-POX). The gel eluant was collected by 5 ml portions the absorption of which was measured at $OD_{280}$ and $OD_{403}$.

(b) Labelling with Isotope ($^{125}I$-PGM)

PGM was labelled with $^{125}I$ according to an oxidative iodination process using chloramine T.

10 μg of PGM was dissolved in 50 μl of a 0.2M phosphate buffer solution (pH 7.0), and 10 μl of 1 mCi of $Na^{125}I$ (carrier-free; N.E.N.) and 50 μg/100 μl of chloramine T solution in a 0.2M phosphate buffer solution were added thereto and, after mixing at room temperature for 30 seconds, 100 μg/100 μl of $Na_2S_2O_5$ solution in a 0.2M phosphate buffer solution was added thereto. Then, 1 mg of $Na^{125}I$ was added thereto and mixed. The thus-obtained $^{125}I$-PGM was purified on Sephadex G-50 (1×30 cm). The thus-prepared $^{125}I$-PGM had a radioactivity of about 1–2 μCi/μg.

(vi) Determining Process 0.1 ml of $^{125}I$-PGM (100 ng 0.17 μCi corresponding to about $2.4\times10^5$ cpm) obtained in (v), 0.1 ml of the pure standard PGM (0.1 μg/ml, 0.2 μg/ml, 0.5 μg/ml, 1 μg/ml, 2.5 μg/ml, 5 μg/ml) obtained in (iv), 0.1 ml of PNA (10 μg/ml), and 0.2 ml of a 0.05M phosphoric acid buffer solution (0.15M NaCl; 0.1% BSA; 0.02% $NaN_3$) were mixed in a 10×75 mm glass tube, and incubated at 25° C. for 1 hour. After completion of the reaction, 0.1 ml of anti-PNA rabbit serum (made by E. Y. Laboratory; 10-times diluted solution) was added to the $^{125}I$-PGM bound to PNA and $^{125}I$-PGM unbound to PNA and, after incubating at 25° C. for 1 hour, the reaction solution was centrifuged at 4° C. for 30 minutes at 3,000 rpm. The radioactivity of a precipitate ($^{125}I$-PGM bound to PNA) was counted to prepare a standard curve (FIG. 1). As is clear from the results thus-obtained, % Bound (B/T) was usually 20 to 25% and 50% inhibition was obtained at a concentration of 0.6 μg/ml.

(vii) Preparation of Insolubilized TAG-Like Material

An excess amount of PGM was added to 100 ml of a 0.01M phosphate buffer solution (pH 7.0) to prepare a suspension. A 0.01N NaOH solution was added thereto to adjust the pH of the suspension to about 11, followed by centrifuging at 3,000 rpm for 20 minutes to recover the supernatant. To this supernatant was dropwise added 0.03N HCl to adjust the pH to 7.0, and centrifugation was again conducted at 3,000 rpm for 20 minutes. The supernatant was dialyzed against a 0.01M phosphate buffer solution (pH 7.0) to prepare a PGM solution. As to the sugar content and protein content of the solution, hexose content was measured to be 5 to 7 mg/ml according to a phenol-sulfuric acid method using glucose as a standard, and protein content was measured to be 1 to 2 mg/ml using BSA as a standard. The PGM solution was subjected to the following radiation-induced polymerization.

The radiation-induced polymerization was conducted as follows. Hydroxyethylmethacrylate (HEMA) (used as monomer) was mixed with the above-described PGM solution in a mixing ratio of 33:67, and the resulting mixture was placed in a 1 cm×15 to 20 cm glass tube and rapidly lyophilized to $-70°$ C. or lower. Subsequently, it was irradiated with $1\times10^6$ rad gamma rays to polymerize the monomer. Each of the thus-fixed PGM materials was prepared by slicing the polymer rod with a thickness of 10 μm to prepare slices of discs.

(viii) Preparation of Insolubilized TAG-Like Material 15 g (dry weight) of CNBr-activated Sepharose 4B (made by Pharmacia AB) was suspended in 3 liters of 0.001N hydrochloric acid and, after allowing to stand for 30 minutes, washed with 1 liter of 0.1M sodium hydrogencarbonate (pH 8.5) on a glass filter to obtain about 50 ml of activated Sepharose. This was suspended in 200 ml of 0.1M sodium hydrogencarbonate (pH 8.5), and 5 ml of a 0.01M phosphate buffer solution (pH 7.7) containing 50 mg of PGM was added thereto followed by reacting at room temperature for 2 hours with stirring at times.

After completion of the reaction, the reaction solution was washed on a glass filter, and the reaction product was added to 200 ml of a 1M monoethanolamine solution (pH 8.5) followed by reacting at room temperature for 2 hours. Then, the reaction solution was washed on a glass filter with 1 liter of a 0.1M acetic acid buffer solution (containing 0.5M NaCl) and 1 liter of a 0.1M boric acid buffer solution (containing 0.5M NaCl) alternately three times.

(viii') Process for Preparing Insolubilized TAG-Like Material (Preparation of PGM-Bead)

10,000 polystyrene beads having a diameter of 6.4 mm manufactured by Precision Plastic Co., Ltd., U.S.A. were washed with a diluted solution of synthetic soap (mamalemon ®, manufactured by Lion Co., Ltd.) at a concentration of 1.5 ml/1 l of distilled water and then with distilled water. Further, after dipping them in 0.5M NaOH aqueous solution for 3 days the beads were washed thoroughly until the pH of the washing became about 6. The thus-washed 10,000 beads were added in 2.5 liter of 35 (w/v) % PGM solution in 50 mM acetic acid buffer adjusted to pH 4.5 with 10N NaOH, rotated at about 10 rpm for 24 hours, filtered and washed with 8 liter of distilled water four times. Then, the beads were added to 2.5 liter of glutaraldehyde solution of final concentration 1 v/v % in 50 mM sodium phosphate buffer (pH 7), rotated at 10 rpm for 2 hours, filtered and washed with distilled water in the same manner as above. The thus-treated 10,000 beads were added to 2.5 liter of 1M glycine solution in 50 mM sodium phosphate buffer (pH 7.0), rotated at 10 rpm for 2 hours, filtered and washed with distilled water in the same manner as above followed by drying at 37° C. overnight to obtain PGM-beads. The surface area of beads was determined according to Orcinol-$H_2SO_4$ method (M. Schönenberger, et al., Z. Physiol. Chem., 309, 145 (1957)) and the result obtained is 2.7±0.2 μg PGM/bead.

(ix) Preparation of Test Samples 5 ml of blood was collected from each of cancer-suffering patients, patients suffering with other disease, pregnant women and healthy persons using heparin (500 units)-treated syringe, and centrifuged for 10 minutes at 2,000 rpm, and the supernatant was collected to prepare test samples.

EXAMPLE 2

Competitive Process

Figure 2:
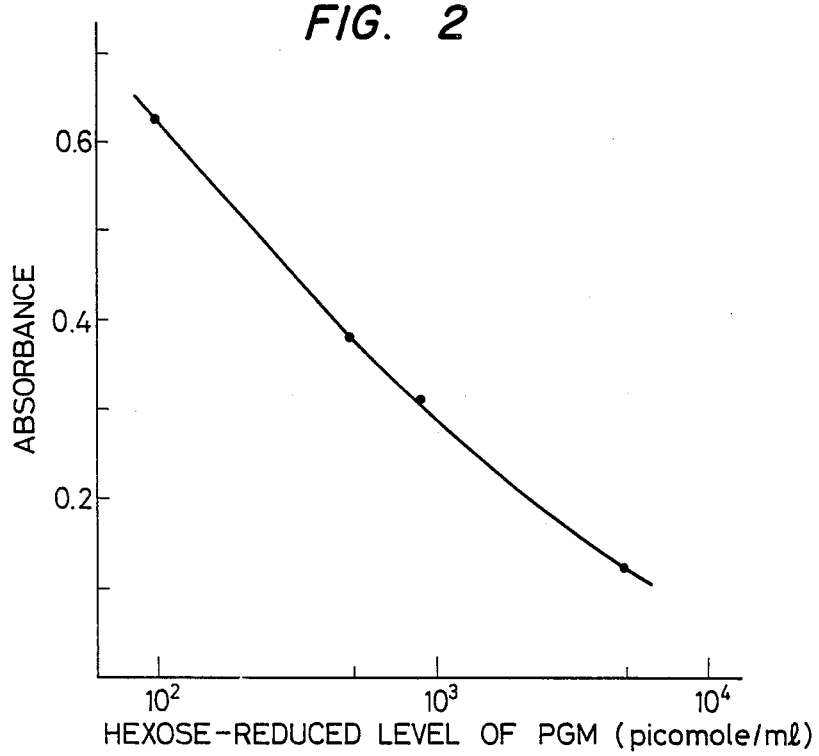
FIG. 2 shown a calibration curve for the competitive process of the present invention.

A slice of disc (insolubilized TAG-like material prepared in (vii)) was placed in 50 μl of PNA-bound peroxidase (labelled lectin prepared in (ii)) and 200 μl of the sample (test sample prepared in (ix)), and incubated at 25° C. for 20 hours. Then, the disc was washed with PBS and placed in 2.0 ml of a saline aqueous solution, and 0.5 ml of a peroxidase material was added thereto followed by incubating at 25° C. for 1 hour. Then, 1.0 ml of 3N hydrochloric acid was added thereto, and the absorbance was measured at 492 nm. At the same time, the absorbance was measured in the same manner except for changing the sample to various concentrations of a standard material (PGM) to prepare a calibration curve (FIG. 2). Further, TAG in the test samples obtained in (ix) was determined using the calibration curve. The results thus-obtained are shown in FIGS. 3 and 4.

Figure 3:
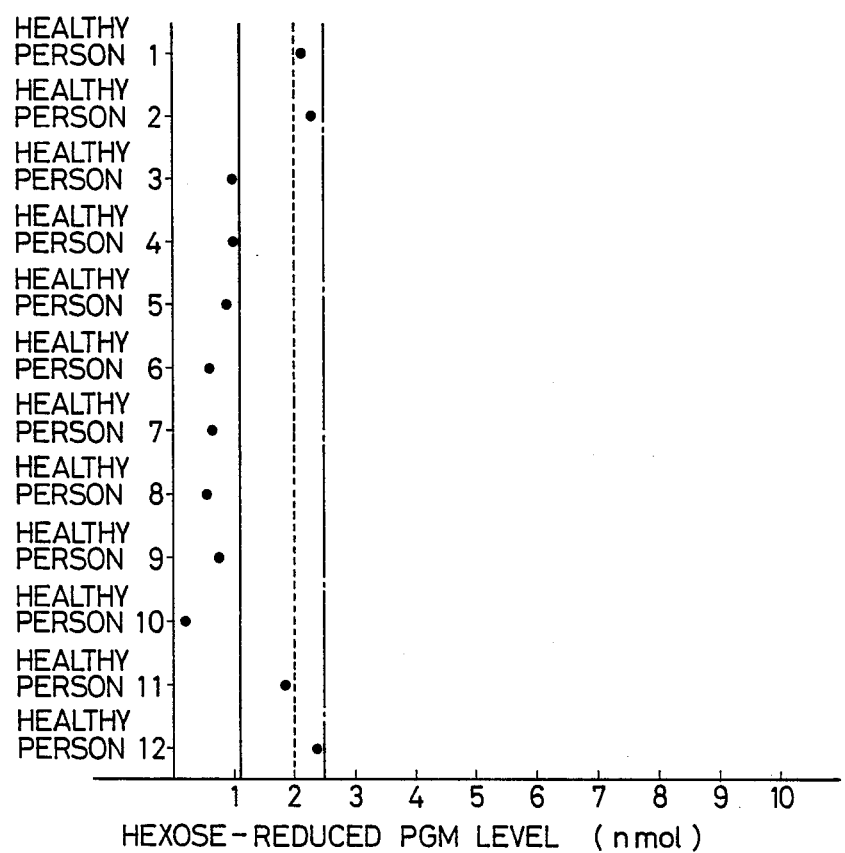
FIG. 3 shows TAG levels of healthy persons measured according to the competitive process of the present invention.
Figure 4:
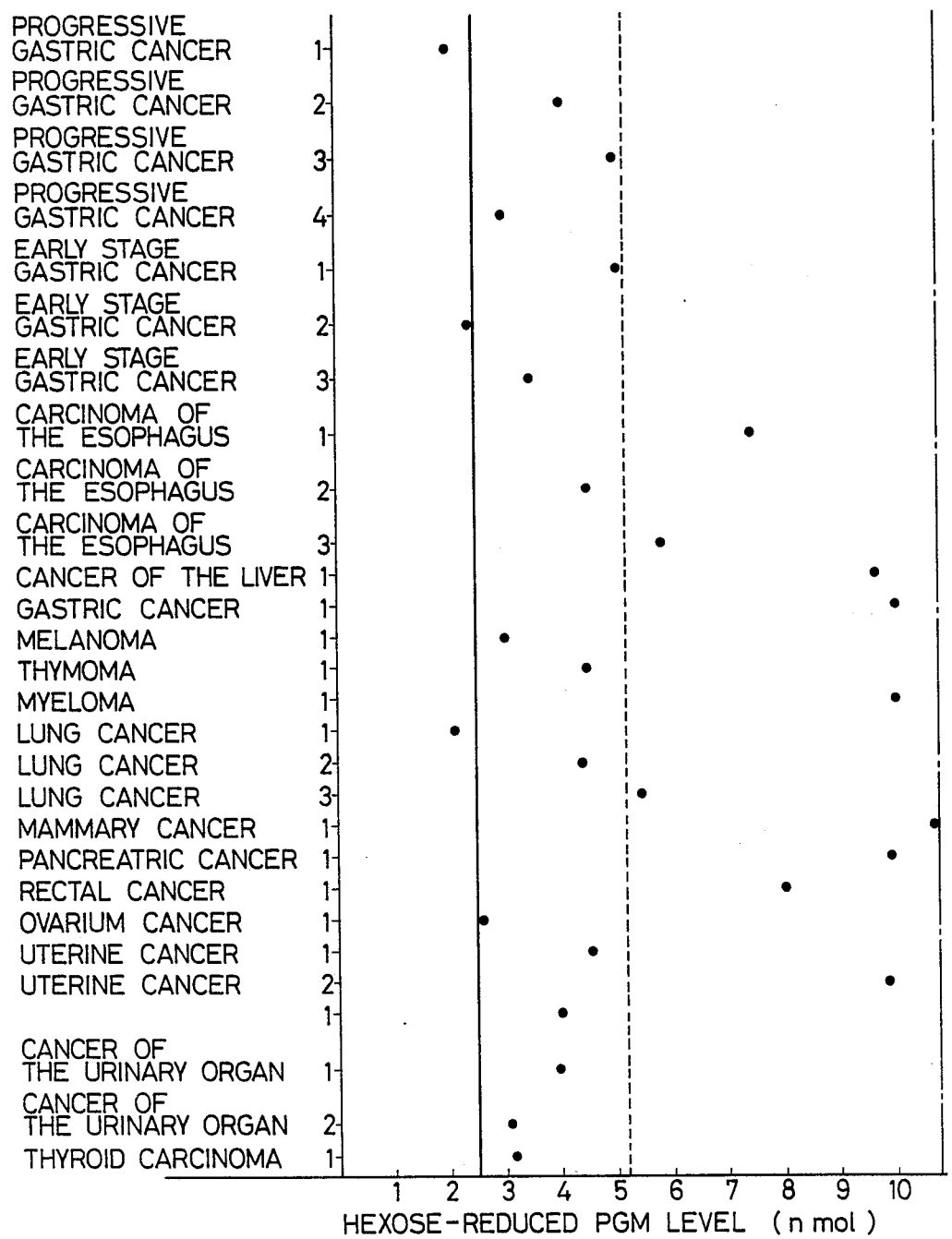
FIG. 4 shows TAG levels of cancerous patients measured according to the competitive process of the present invention.

As is clear from FIGS. 3 and 4, there was a distinct difference in TAG level between healthy persons and patients suffering with various cancers.

EXAMPLE 3

Sandwiching Process

Figure 5:
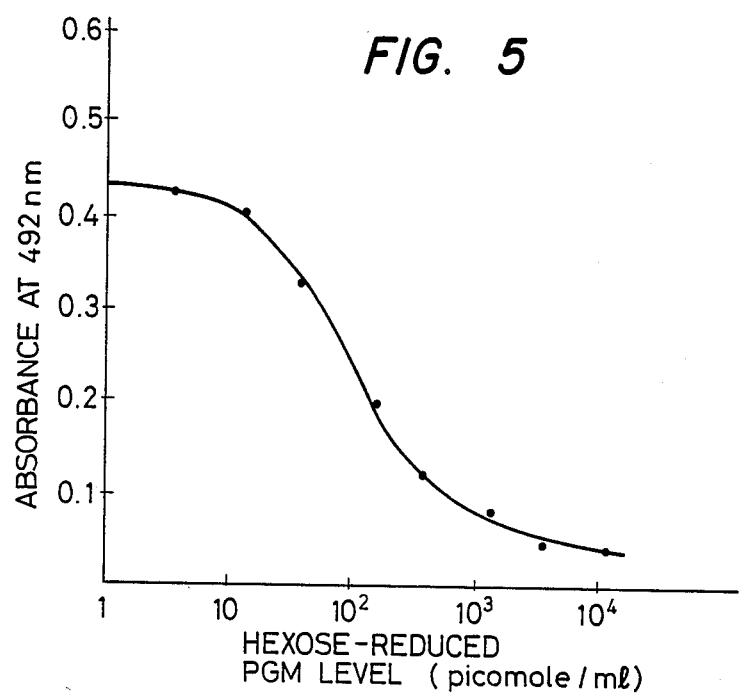
FIG. 5 shows a calibration curve for the sandwiching process of the present invention.

200 μg of PNA-agarose prepared in (iii) was added to 100 μl of a 0.05M phosphate buffer solution (pH 7.0) containing dissolved therein 1 to 10 μg/ml of PGM, and incubation was conducted at 25° C. for 1 hour under stirring. After washing the reaction solution three times with a 0.05M phosphate buffer solution (pH 7.0), 6 μg of PNA labelled with peroxidase obtained in Example 1, (ii) and 100 μl of a 0.05M phosphate buffer solution (pH 7.0) were added thereto followed by incubating at 25° C. for 1 hour under stirring. After centrifuging at 3,000 rpm for 10 minutes, the precipitate was recovered and washed three times with a 0.05M phosphate buffer solution (pH 7.0), and the absorbance was measured at 492 nm. The results thus-obtained are shown in FIG. 5.

EXAMPLE 4

Competitive Process

100 μl of a sample (test sample obtained according to the process (ix) above) was placed in a test tube to which 500 μl of 0.3M tris-HCl buffer (pH 7.4) containing therein a final 0.22 w/v % of gelatin, 5 mM $CaCl_2$ and 5 mM $MgCl_2$ was added. One PGM-bead (insolubilized TAG-like material prepared according to the process (viii')) and 100 μl of lectin-peroxidase (the lyophilized labelled lectin prepared according to the process (ii') above at a concentration of 1 mg/l of the above-described tris-Hcl buffer) were added to the sample and after stirring the mixture was incubated for 24 hours. The reaction mixture was removed using an aspirator and the bead was washed with 2 ml of physiological saline solution followed by removing the washing using an aspirator. This washing operation was repeated three times.

60 mg of ortho-phenylenediamine was dissolved in 20 ml of 0.2M McIlevein buffer (pH 5.8) and $H_2O_2$ was added to the resulting solution at a final concentration of 0.02 v/v %, and the mixture was stirred to form a coloring agent.

Figure 6:
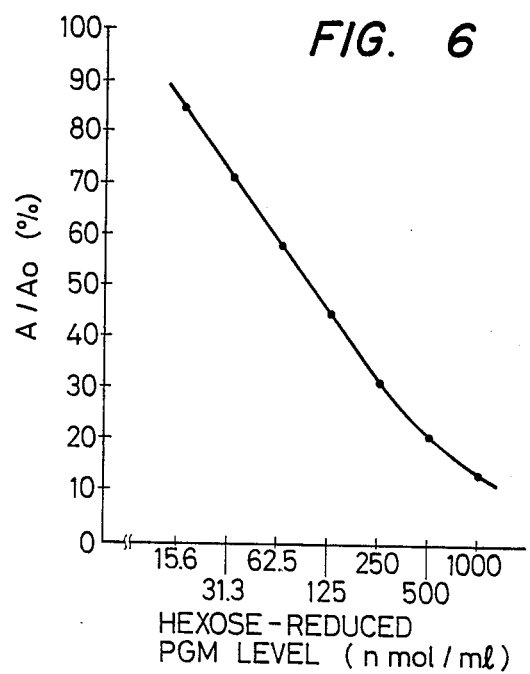
FIG. 6 shows a calibration curve for competitive process of the present invention.
Figure 7A:
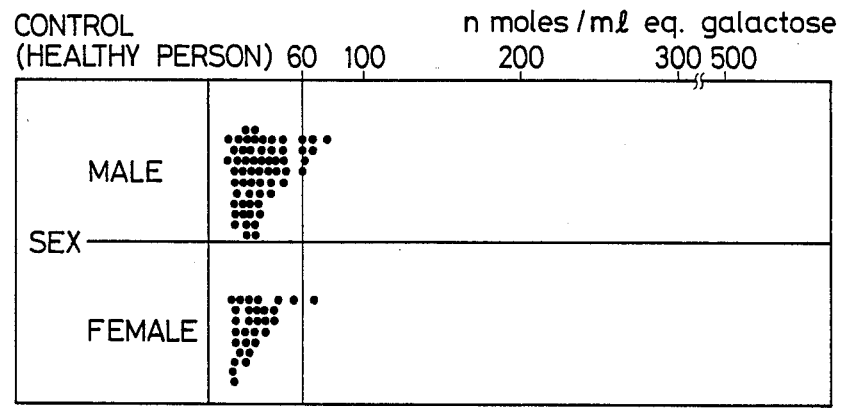
FIG. 7a shows TAG levels of healthy persons measured according to the competitive process of the present invention.
Figure 7B:
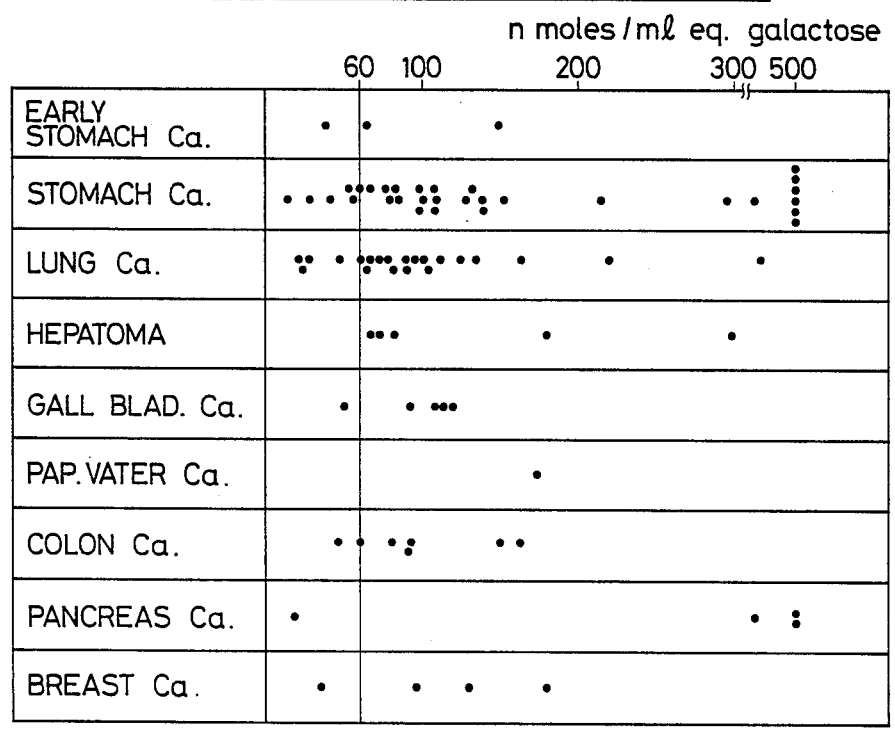
FIGS. 7b and 7c show TAG levels of patients with cancers measured according to the competitive process of the present invention.
Figure 7C:
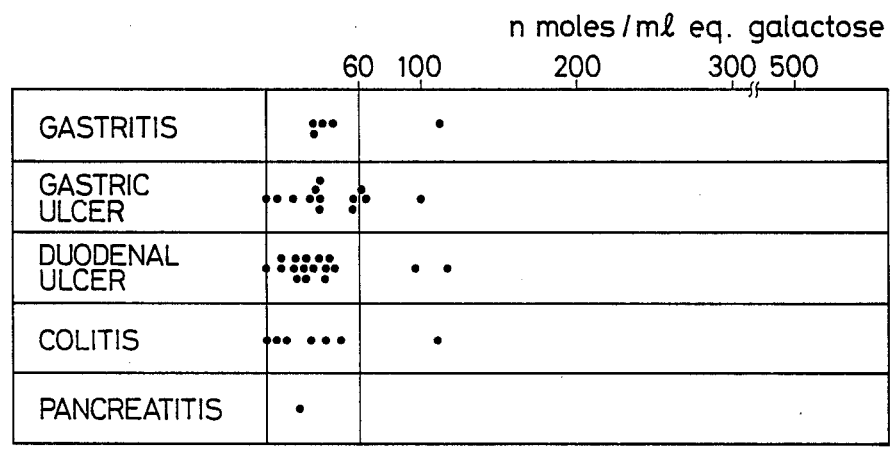

In a test tube were placed 2 ml of physiological saline solution and 500 μl of the coloring agent as well as the washed bead followed by incubating at room temperature for 30 minutes. Then, the enzymatic reaction was stopped with 1 ml of 3N HCl. The optical density of the reaction mixture was measured at 492 nm. At the same time, absorbance was measured in the same manner except for changing the sample to various concentrations of a standard material (PGM) to prepare a calibration curve (FIG. 6). Further, TAG in the test samples obtained in (ix) above was determined using the calibration curve. The results obtained are shown in FIGS. 7a, 7b, 7c and 7d.

While the invention has been described in detail and with reference to specific embodiments thereof, it will be apparent to one skilled in the art that various changes and modifications can be made therein without departing from the spirit and scope thereof.

What is claimed is:

1. A process for determining tumor-associated glycolinkage (TAG), which comprises (1) centrifuging body fluid to separate cells and cell debris contained therein and collecting the supernatant, (2) competitively reacting body fluid TAG contained in the supernatant and a definite quantity of an insolublized TAG or TAG-like material with a definite quantity of labelled lectin, (3) separating the insolubilized TAG or TAG-like material bound to labelled lectin and unbound lectin from each other, and (4) measuring the labelling agent activity of either of them, wherein said TAG-like material is galactose-($\beta 1\rightarrow 3$ or $\beta 1\rightarrow 4$)-N-acetylglucosamine, galactose-($\beta 1\rightarrow 3$ or $\beta 1\rightarrow 4$)-N-acetylgalactosamine or a sugar derivative containing said glycolinkage as a terminal group and wherein said labelled lectin is a lectin which can combine specifically with galactose-($\beta 1\rightarrow 3$ or $\beta 1\rightarrow 4$)-N-acetylglucosamine or galactose-($\beta 1\rightarrow 3$ or $\beta 1\rightarrow 4$)-N-acetylgalactosamine.

2. The determining process as described in claim 1, wherein said labelled lectin is labelled with an enzyme, a fluorescent material or a radioactive material.

3. the determining process as described in claim 1, wherein said body fluid is blood, cell tissue fluid, lymph fluid, thorax fluid, abdominal fluid, amniotic fluid, gastric juice, urine, pancreatic juice, cerebrospinal fluid or saliva.

4. The determining process as described in claim 1, wherein the TAG-like material for said insolubilized TAG-like material is selected from the group consisting of glycoprotein of human gastric mucin, glycoprotein obtained by removing terminal fucose from sulfated glycoprotein of porcine gastric mucous membrane, human IgG glycoprotein or the asialo derivative thereof, bovine IgG glycoprotein, asialo derivative of glycoprotein of porcine thyroglobulin glycolinkage B, glycoprotein of ovomucoid $\beta$-subunit, glycoprotein B-1 of human IgE or the asialo derivative thereof, asialo derivative of glycoprotein B-2 or B-3 of human IgE and asialo derivative of glycoprotein II-C of human $IgA_1$, asialo derivative of glycoprotein II-B or II-A of human $IgA_1$, asialo derivative of human transferrin glycoprotein, asialo derivative of bovine fetuin glycoprotein, deasialo derivative of glycoprotein participating in uptake of asialo glycoprotein of rabbit liver cell protoplasmic membrane, sulfated glycoprotein of porcine gastric mucosa, asialo derivative of human $\alpha_1$ acidic glycoprotein, asialo derivative of glycofolin, glycoprotein of T-antigen, glycopetide of T-antigen, asialo $GM_1=AM_1$ and glycolipids of bovine erythrocyte; said labelling material for lectin is selected from the group consisting of glucoamylase, glucose oxidase, peroxidase, alkaline phosphatase, $\beta$-galactosidase, active fragment of hemoctapeptide, $^{125}I$, $^{131}I$ and radioactive tritium; said lectin is selected from the group consisting of peanut lectin and castor bean lectin; and the insoluble carrier for said insolubilized TAG or insolubilized TAG-like material is selected from the group consisting of cellulose powder, Sephadex, Sepharose, polystyrene, filter paper, carboxymethyl cellulose, ion-exchange resin, dextran, plastic film, plastic tube, nylon, glass beads, silk, polyamine-methyl vinyl ethermaleic acid copolymer, amino acid copolymer, and ethylenemaleic acid copolymer.

5. The determining process as described in claim 1, wherein the TAG-like material for said insolubilized TAG-like material is selected from the group consisting of glycoprotein of human gastric mucin, glycoprotein obtained by removing terminal fucose from sulfated glycoprotein of porcine gastric mucous membrane, human IgG glycoprotein or the asialo derivative thereof, bovine IgG glycoprotein, asialo derivative of glycoprotein of porcine thyroglobulin glycolinkage B, glycoprotein of ovomucoid β-subunit, glycoprotein B-1 of human IgE or the asialo derivative thereof, asialo derivative of glycoprotein B-2 or B-3 of human IgE and asialo derivative of glycoprotein II-C of human IgA$_1$, asialo derivative of glycoprotein II-B or II-A of human IgA$_1$, asialo derivative of human transferrin glycoprotein, deasialo derivative of glycoprotein participating in uptake of asialo glycoprotein of rabbit liver cell protoplasmic membrane, sulfated glycoprotein of procine gastric mucosa, asialo derivative of human α$_1$ acidic glycoprotein, asialo derivative of glycofolin, glycoprotein of T-antigen, glycopeptide of T-antigen, asialo GM$_1$=AM$_1$ and glycolipids of bovine erythrocyte; said labelling material for lectin is selected from the group consisting of glucoamylase, glucose oxidase, peroxidase, alkaline phosphatase, β-galactoxidase, active fragment of hemoctapeptide, $^{125}$I, $^{131}$I, and radioactive tritium; said lectin is selected from the group consisting of peanut lectin and castor bean lectin and said insolubilized TAG or insolubilized TAG-like material is a polymeric matrix prepared by irradiating an aqueous dispersion of a polymerizable monomer containing TAG or TAG-like material with ionizing radiation to polymerize said monomer, said aqueous dispersion being selected from the group consisting of an aqueous dispersion of a mixture of hydrophobic polymerizable monomer [A] and water-soluble polymer [B], an aqueous dispersion of a mixture of hydrophobic polymerizable monomer [A] and hydrophilic polymerizable monomer [C], an aqueous dispersion of a mixture of hydrophobic polymerizable monomer [A] and surfactant [D], and an aqueous dispersion of hydrophilic polymerizable monomer [C] wherein said hydrophobic polymerizable monomer is selected from the group consisting of glycidyl methacrylate, ethylene glycol dimethacrylate, diethylene glycol dimethacrylate, triethylene glycol dimethacrylate, trimethylolpropane trimethacrylate, polyethylene glycol 200 dimethacrylate, dipropylene glycol dimethacrylate, 1,4-butylene glycol dimethacrylate, 1,6hexane glycol dimethacrylate, methoxydiethylene glycol dimethacrylate, methyl methacrylate, ethyl methacrylate, butyl methacrylate, and the corresponding acrylates thereof; said water-soluble polymer [B] is selected from the group consisting of polyvinyl pyrrolidone, polymethacrylic acid, polyacrylic acid, polyvinyl alcohol, hydroxypropyl cellulose and gum arabic; said hydrophilic polymerizable monomer is selected from the group consisting of 2-hydroxyethyl methacrylate, methoxytetraethylene glycol methacrylate, methoxypolyethylene glycol 400 methacrylate, methoxypolyethylene glycol 1000 methacrylate, polyethylene glycol 400 dimethacrylate, polyethylene glycol 600 dimethacrylate, and the corresponding acrylates thereof and methacrylic acid, acrylamide, and N-vinyl-2-pyrrolidone; and said surfactant [D] is selected from the group consisting of sodium laurylsulfate, potassium oleate, sodium oleate, sorbitan monolaurate, sorbitan monostearate, sorbitan monooleate, propylene glycol monolaurate, oleic acid, sodium dodecylbenzenesulfonate.

6. The determining process as described in claim 1, wherein said insolubilized TAG-like material is a polymer matrix prepared by irradiating an aqueous dispersion of hydroxyethyl methacrylate containing sulfated glycoprotein of procine gastric mucosa with γ-ray and said labelled lectin is peroxidase-labelled peanut lectin.

7. The determining process as described in claim 1, wherein said insolubilized TAG-like material is polystyrene bead-insolubilized sulfated glycoprotein of porcine gastric mucosa and said labelled lectin is peroxidase-labelled peanut lectin.

8. A process for determining tumor-associated glycolinkage (TAG), which comprises (1) centrifuging body fluid to separate cells and cell debris contained therein and collecting the supernatant, (2) competitively reacting body fluid TAG contained in the supernatant and a definite quantity of labelled TAG or labelled TAG-like material with a definite quantity of lectin or unsolubilized lectin, (3) separating the labelled TAG or labelled TAG-like material bound to lectin or insolubilized lectin and unbound labelled TAG or labelled TAG-like material from each other, and (4) measuring the labelling agent activity of either of them, wherein said TAG-like material is galactose-(β1→3 or β1→4)-N-acetylglucosamine, galactose-(β1→3 or β1→4)-N-acetylgalactosamine or a sugar derivative containing said glycolinkage as a terminal group and wherein said lectin or insolubilized lectin is a lectin which can combine specifically with galactose-(β1→3 or β1→4)-N-acetylglucosamine or galactose-(β1→3 or β1→4)-N-acetylgalactosamine.

9. The determining process as described in claim 8, wherein said labelled TAG or labelled TAG-like material is labelled with an enzyme, a fluorescent material or a radioactive material.

10. The determining process as described in claim 8, wherein said body fluid is blood, cell tissue fluid, lymph fluid, thorax fluid, abdominal fluid, amniotic fluid, gastric juice, urine, pancreatic juice, cerebrospinal fluid or saliva.

11. The determining process as described in claim 8, wherein the TAG-like material of said labelled TAG-like material is selected from the group consisting of glycoprotein of human gastric mucin, glycoprotein obtained by removing terminal fucose from sulfated glycoprotein of porcine gastric mucous membrane, human IgG glycoprotein or the asialo derivative thereof, bovine IgG glycoprotein, asialo derivative of glycoprotein of porcine thyroglobulin glycolinkage B, glycoprotein of ovomucoid β-subunit, glycoprotein B-1 of human IgE or the asialo derivative thereof, asialo derivative of glycoprotein B-2 or B-3 of human IgE and asialo derivative of glycoprotein II-C of human IgA$_1$, asialo derivative of glycoprotein II-B or II-A of human IgA$_1$, asialo derivative of human transferrin glycoprotein, asialo derivative of bovine fetuin glycoprotein, deasialo derivative of glycoprotein participating in uptake of asialo glycoprotein of rabbit liver cell protoplasmic membrane, sulfated glycoprotein of porcine gastric mucosa, asialo derivative of human α$_1$ acidic glycoprotein, asialo derivative of glycofolin, glycoprotein of T-antigen, glycopeptide of T-antigen, asialo $Gm_1=AM_1$ and glycolipids of bovine erythrocyte; said labelling material for TAG or TAG-like material is selected from the group consisting of glucoamylase, glucose oxidase, peroxidase, alkaline phosphatase, $\beta$-galactosidase, active fragment of hemoctapeptide, $^{125}I$, $^{131}I$ and radioactive tritium; said lectin is selected from the group consisting of peanut lectin and castor bean lectin; and the insoluble carrier for said insolubilized lectin is selected from the group consisting of cellulose powder, Sephadex, Sepharose, polystyrene, filter paper, carboxymethyl cellulose, ion-exchange resin, dextran, plastic film, plastic tube, nylon, glass beads, silk, polyaminemethyl vinyl ether-maleic acid copolymer, amino acid copolymer, and ethylene-maleic acid copolymer.

12. A process for determining tumor-associated glycolinkage (TAG), which comprises (1) centrifuging body fluid to separate cells and cell debris contained therein and collecting the supernatant (2) reacting body fluid TAG contained in the supernatant with an insolubilized lectin to form a TAG-insolubilized lectin complex, (3) reacting this complex with a definite quantity of labelled lectin, (4) separating the complex bound to the labelled lectin and unbound labelled lectin from each other, and (5) measuring the labelling agent activity of either of them, wherein said insolubilized lectin and labelled lectin is a lectin which can combine specifically with galactose-($\beta1\rightarrow3$ or $\beta1\rightarrow4$)-N-acetylglucosamine or galactose-($\beta1\rightarrow3$ or $\beta1\rightarrow4$)-N-acetylgalactosamine.

13. The determining process as described in claim 12, wherein said labelled lectin is labelled with an enzyme, a fluorescent material or a radioactive material.

14. The determining process as described in claim 12, wherein said body fluid is blood, cell tissue fluid, lymph fluid, thorax fluid, abdominal fluid, amniotic fluid, gastric juice, urine, pancreatic juice, cerebrospinal fluid, or saliva.

15. The determining process as described in claim 12, wherein the lectin of said insolubilized lectin or labelled lectin is selected from the group consisting of peanut lectin and castor bean lectin; the labelling material for said labelled lectin is selected from the group consisting of glucoamylase, glucose oxidase, peroxidase, alkaline phosphatase, $\beta$-galactosidase, active fragment of hemoctapeptide, $^{125}I$, $^{131}I$ and radioactive tritium, and the insoluble carrier for said insolubilized lectin is selected from the group consisting of cellulose powder, Sephadex, Sepharose, polystyrene, filter paper, carboxymethyl cellulose, ion-exchange resin, dextran, plastic film, plastic tube, nylon, glass beads, silk, polyaminemethyl vinyl ether-maleic acid copolymer, amino acid copolymer and ethylene-maleic acid copolymer.

16. The determining process as described in claim 12, wherein the lectin of said insolubilized lectin or labelled lectin is selected from the group consisting of peanut lectin and castor bean lectin; the labelling material for said labelled lectin is selected from the group consisting of glucoamylase, glucose oxidase, peroxidase, alkaline phosphatase, $\beta$-galactosidase, active fragment of hemoctapeptide, $^{125}I$, $^{131}I$ and radioactive tritium; the insoluble carrier for said insolubilized lectin is selected from the group consisting of cellulose powder, Sephadex, Sepharose, polystyrene, filter paper, carboxymethyl cellulose, ion-exchange resin, dextran, plastic film, plastic tube, nylon, glass beads, silk, polyaminemethyl vinyl ether-maleic acid copolymer, amino acid copolymer and etylene-maleic acid copolymer, and said insolubilized lectin is a polymeric matrix prepared by irradiating an aqueous dispersion of a polymerizable monomer containing lectin with ionizing radiation to polymerize said monomer, said aqueous dispersion being selected from the group consisting of an aqueous dispersion of a mixture of hydrophobic polymerizable monomer [A] and water-soluble polymer [B], an aqueous dispersion of a mixture of hydrophobic polymerizable monomer [A] and hydrophilic polymerizable monomer [C], an aqueous dispersion of a mixture of hydrophobic polymerizable monomer [A] and surfactant [D], and an aqueous dispersion of hydrophilic polymerizable monomer [C] wherein said hydrophobic polymerizable monomer is selected from the group consisting of glycidyl methacrylate, ethylene glycol dimethacrylate, diethylene glycol dimethacrylate, triethylene glycol dimethacrylate, trimethylolpropane trimethacrylate, polyethylene glycol 200 dimethacrylate, dipropylene glycol dimethacrylate, methoxydiethylene glycol dimethacrylate, methyl methacrylate, ethyl methacrylate, butyl methacrylate, and the corresponding acrylates thereof; said water-soluble polymer [B] is selected from the group consisting of polyvinyl pyrrolidone, polymethacrylic acid, polyacrylic acid, polyvinyl alcohol, hydroxypropyl cellulose and gum arabic; said hydrophilic polymerizable monomer is selected from the group consisting of 2-hydroxyethyl methacrylate, methoxytetraethylene glycol methacrylate, methoxypolyethylene glycol 400 methacrylate, methoxypolyethylene glycol 1000 methacrylate, polyethylene glycol 400 dimethacrylate, polyethylene glycol 600 dimethacrylate, and the corresponding acrylates thereof and methacrylic acid, acrylamide, and N-vinyl-2-pyrrolidone; and said surfactant [D] is selected from the group consisting of sodium laurylsulfate, potassium oleate, sodium oleate, sorbitan monolaurate, sorbitan monostearate, sorbitan monooleate, propylene glycol monolaurate, oleic acid, and sodium dodecylbenzenesulfonate.

17. The determining process as described in claim 12, wherein said labelled lectin is peroxidase-labelled peanut lectin and said insolubilized lectin is sepharose-insolubilized peanut lectin.

18. The determining process as described in claims 1, 8 or 12, wherein said body fluid is blood, cell tissue fluid, lymph fluid, thorax fluid, abdominal fluid, amniotic fluid, gastric juice, pancreatic juice, cerebrospinal fluid or saliva.

19. The determining process as described in claim 18, wherein said body fluid is blood.

20. A method for diagnosing cancer, which comprises measuring the level of tumor-associated glycolinkage in body fluid of a subject according to the method described in any one of claims 1, 8 and 12 and comparing the thus-measured level with that of a person in normal health.

* * * * *